(12) United States Patent
Nita et al.

(10) Patent No.: US 8,062,566 B2
(45) Date of Patent: Nov. 22, 2011

(54) METHOD OF MANUFACTURING AN ULTRASOUND TRANSMISSION MEMBER FOR USE IN AN ULTRASOUND CATHETER DEVICE

(75) Inventors: Henry Nita, Redwood City, CA (US); Jeff Sarge, Fremont, CA (US); Simon Nguyen, San Jose, CA (US); Richard Spano, Gilroy, CA (US)

(73) Assignee: Flowcardia, Inc., Sunnyvale, CA (US)

( * ) Notice: Subject to any disclaimer, the term of this patent is extended or adjusted under 35 U.S.C. 154(b) by 823 days.

(21) Appl. No.: 11/493,430

(22) Filed: Jul. 25, 2006

(65) Prior Publication Data
US 2007/0038158 A1 Feb. 15, 2007

Related U.S. Application Data

(62) Division of application No. 10/410,617, filed on Apr. 8, 2003, now Pat. No. 7,220,233.

(51) Int. Cl.
| | |
|---|---|
| *B28B 11/18* | (2006.01) |
| *B28B 17/00* | (2006.01) |
| *A61H 1/00* | (2006.01) |
| *A61H 1/02* | (2006.01) |
| *A61G 5/00* | (2006.01) |
| *A61M 25/00* | (2006.01) |

(52) U.S. Cl. ....... 264/162; 29/DIG. 19; 601/2; 604/523; 604/530

(58) Field of Classification Search .................. None
See application file for complete search history.

(56) References Cited

U.S. PATENT DOCUMENTS

| | | | |
|---|---|---|---|
| 3,433,226 A | 3/1969 | Boyd | |
| 3,565,062 A | 2/1971 | Kuris | |
| 3,631,848 A | 1/1972 | Muller | |
| 3,823,717 A | 7/1974 | Pohlman et al. | |
| 3,896,811 A | 7/1975 | Storz | |
| 4,016,882 A | 4/1977 | Broadwin et al. | |
| 4,033,331 A | 7/1977 | Guss et al. | |

(Continued)

FOREIGN PATENT DOCUMENTS

DE 2256127 5/1974

(Continued)

OTHER PUBLICATIONS

Feninat et al., Shape Memory Materials for Biomedical Applications, Advanced Engineering Materials, Mar. 13, 2002, vol. 4 No. 3, pp. 91-104, http://dx.doi.org/10.1002/1527-2648(200203)4:3<91::AID-ADEM91>3.0.00;2-B.*

(Continued)

*Primary Examiner* — Christina Johnson
*Assistant Examiner* — Benjamin Schiffman
(74) *Attorney, Agent, or Firm* — Knobbe, Martens, Olson & Bear LLP

(57) ABSTRACT

Ultrasound catheter devices and methods provide enhanced disruption of blood vessel obstructions. Generally, ultrasound catheters include an elongate flexible catheter body with one or more lumens, an ultrasound transmission member extending longitudinally through the catheter body lumen and a distal head coupled with the transmission member and positioned adjacent the distal end of the catheter body for disrupting occlusions. Improved features of ultrasound catheters include prevention of independent rotation of the ultrasound transmission member, a safety anchor for the distal head, a one-piece transmission member/distal head and the like.

8 Claims, 9 Drawing Sheets

U.S. PATENT DOCUMENTS

| | | | |
|---|---|---|---|
| 4,136,700 A | 1/1979 | Broadwin et al. | |
| 4,337,090 A | 6/1982 | Harrison | |
| 4,417,578 A | 11/1983 | Banko | |
| 4,425,115 A | 1/1984 | Wuchinich | |
| 4,486,680 A | 12/1984 | Bonnet et al. | |
| 4,505,767 A | 3/1985 | Quin | |
| 4,565,589 A | 1/1986 | Harrison | |
| 4,572,184 A | 2/1986 | Stohl et al. | |
| 4,664,112 A | 5/1987 | Kensey et al. | |
| 4,665,906 A | 5/1987 | Jervis | |
| 4,679,558 A | 7/1987 | Kensey et al. | |
| 4,700,705 A | 10/1987 | Kensey et al. | |
| 4,721,117 A | 1/1988 | Mar et al. | |
| 4,750,902 A | 6/1988 | Wuchinich et al. | |
| 4,808,153 A | 2/1989 | Parisi | |
| 4,811,743 A | 3/1989 | Stevens | |
| 4,827,911 A | 5/1989 | Broadwin et al. | |
| 4,838,853 A | 6/1989 | Parisi | |
| 4,854,325 A | 8/1989 | Stevens | |
| 4,870,953 A | 10/1989 | DonMicheal et al. | |
| 4,886,060 A | 12/1989 | Wiksell | |
| 4,920,954 A | 5/1990 | Alliger et al. | |
| 4,923,462 A | 5/1990 | Stevens | |
| 4,924,863 A | 5/1990 | Sterzer | |
| 4,931,047 A | 6/1990 | Broadwin et al. | |
| 4,936,281 A | 6/1990 | Stasz | |
| 4,936,845 A | 6/1990 | Stevens | |
| 5,000,185 A | 3/1991 | Yock | |
| 5,015,227 A | 5/1991 | Broadwin et al. | |
| 5,026,384 A | 6/1991 | Farr et al. | |
| 5,046,503 A | 9/1991 | Schneiderman | |
| 5,053,008 A | 10/1991 | Bajaj | |
| 5,058,570 A | 10/1991 | Idemoto et al. | |
| 5,076,276 A | 12/1991 | Sakurai et al. | |
| 5,091,205 A | 2/1992 | Fan | |
| 5,100,423 A | 3/1992 | Fearnot | |
| 5,114,414 A | 5/1992 | Buchbinder | |
| 5,116,350 A | 5/1992 | Stevens | |
| 5,127,917 A | 7/1992 | Niederhauser et al. | |
| 5,156,143 A | 10/1992 | Bocquet et al. | |
| 5,163,421 A | 11/1992 | Bernstein et al. | |
| 5,180,363 A | 1/1993 | Idemoto et al. | |
| 5,195,955 A | 3/1993 | Don Michael | |
| 5,215,614 A * | 6/1993 | Wijkamp et al. | 156/153 |
| 5,221,255 A | 6/1993 | Mahurkar et al. | |
| 5,226,421 A | 7/1993 | Frisbie et al. | |
| 5,234,416 A | 8/1993 | Macaulay et al. | |
| 5,238,004 A * | 8/1993 | Sahatjian et al. | 600/585 |
| 5,242,385 A | 9/1993 | Strukel | |
| 5,243,997 A | 9/1993 | Uflacker et al. | |
| 5,248,296 A | 9/1993 | Alliger | |
| 5,255,669 A | 10/1993 | Kubota et al. | |
| 5,267,954 A | 12/1993 | Nita | |
| 5,269,291 A | 12/1993 | Carter | |
| 5,269,297 A | 12/1993 | Weng et al. | |
| 5,269,793 A | 12/1993 | Simpson | |
| 5,287,858 A | 2/1994 | Hammerslag et al. | |
| 5,290,229 A | 3/1994 | Paskar | |
| 5,304,115 A * | 4/1994 | Pflueger et al. | 604/22 |
| 5,304,131 A | 4/1994 | Paskar | |
| 5,312,328 A | 5/1994 | Nita et al. | |
| 5,324,255 A | 6/1994 | Passafaro et al. | |
| 5,324,260 A | 6/1994 | O'Neill et al. | |
| 5,325,860 A | 7/1994 | Seward et al. | |
| 5,326,342 A | 7/1994 | Pflueger et al. | |
| 5,341,818 A | 8/1994 | Abrams et al. | |
| 5,342,292 A | 8/1994 | Nita et al. | |
| 5,344,395 A | 9/1994 | Whalen et al. | |
| 5,346,502 A | 9/1994 | Estabrook et al. | |
| 5,362,309 A | 11/1994 | Carter | |
| 5,368,557 A | 11/1994 | Nita et al. | |
| 5,368,558 A | 11/1994 | Nita | |
| 5,378,234 A | 1/1995 | Hammerslag et al. | |
| 5,380,274 A * | 1/1995 | Nita | 604/22 |
| 5,380,316 A | 1/1995 | Aita et al. | |
| 5,382,228 A | 1/1995 | Nita et al. | |
| 5,383,460 A | 1/1995 | Jang et al. | |
| 5,389,096 A | 2/1995 | Aita et al. | |
| 5,397,293 A | 3/1995 | Alliger et al. | |
| 5,397,301 A | 3/1995 | Pflueger et al. | |
| 5,405,318 A | 4/1995 | Nita | |
| 5,409,483 A | 4/1995 | Campbell et al. | |
| 5,417,672 A | 5/1995 | Nita et al. | |
| 5,417,703 A | 5/1995 | Brown et al. | |
| 5,427,118 A | 6/1995 | Nita et al. | |
| 5,431,168 A | 7/1995 | Webster, Jr. | |
| 5,431,663 A | 7/1995 | Carter | |
| 5,443,078 A | 8/1995 | Uflacker | |
| 5,447,509 A | 9/1995 | Mills et al. | |
| 5,449,369 A | 9/1995 | Imran | |
| 5,451,209 A | 9/1995 | Ainsworth et al. | |
| 5,465,733 A | 11/1995 | Hinohara et al. | |
| 5,480,379 A | 1/1996 | La Rosa | |
| 5,484,398 A | 1/1996 | Stoddard | |
| 5,487,757 A | 1/1996 | Truckai et al. | |
| 5,507,738 A | 4/1996 | Ciervo | |
| 5,527,273 A | 6/1996 | Manna et al. | |
| 5,540,656 A | 7/1996 | Pflueger et al. | |
| 5,542,917 A | 8/1996 | Nita et al. | |
| 5,597,882 A | 1/1997 | Schiller et al. | |
| 5,607,421 A | 3/1997 | Jeevanandam et al. | |
| 5,611,807 A | 3/1997 | O'Boyle | |
| 5,618,266 A | 4/1997 | Liprie | |
| 5,626,593 A | 5/1997 | Imran | |
| 5,658,282 A | 8/1997 | Daw et al. | |
| 5,695,460 A | 12/1997 | Siegel et al. | |
| 5,695,507 A | 12/1997 | Auth et al. | |
| 5,715,825 A | 2/1998 | Crowley | |
| 5,720,724 A | 2/1998 | Ressemann et al. | |
| 5,728,062 A | 3/1998 | Brisken | |
| 5,738,100 A | 4/1998 | Yagami et al. | |
| 5,797,876 A | 8/1998 | Spears et al. | |
| 5,816,923 A | 10/1998 | Milo et al. | |
| 5,827,203 A | 10/1998 | Nita | |
| 5,830,222 A | 11/1998 | Makower | |
| 5,895,397 A | 4/1999 | Jang et al. | |
| 5,902,287 A | 5/1999 | Martin | |
| 5,916,192 A | 6/1999 | Nita et al. | |
| 5,935,142 A | 8/1999 | Hood | |
| 5,944,737 A | 8/1999 | Tsonton et al. | |
| 5,957,882 A * | 9/1999 | Nita et al. | 604/22 |
| 5,957,899 A | 9/1999 | Spears et al. | |
| 5,964,223 A | 10/1999 | Baran | |
| 5,967,984 A | 10/1999 | Chu et al. | |
| 5,971,949 A | 10/1999 | Levin et al. | |
| 5,976,119 A | 11/1999 | Spears et al. | |
| 5,989,208 A * | 11/1999 | Nita | 604/22 |
| 5,997,497 A | 12/1999 | Nita et al. | |
| 6,004,280 A | 12/1999 | Buck et al. | |
| 6,007,499 A | 12/1999 | Martin et al. | |
| 6,007,514 A | 12/1999 | Nita | |
| 6,024,764 A * | 2/2000 | Schroeppel | 606/198 |
| 6,030,357 A | 2/2000 | Daoud et al. | |
| 6,051,010 A | 4/2000 | DiMatteo et al. | |
| 6,113,558 A | 9/2000 | Rosenschein et al. | |
| 6,123,698 A | 9/2000 | Spears et al. | |
| 6,149,596 A | 11/2000 | Bancroft | |
| 6,165,127 A | 12/2000 | Crowley | |
| 6,165,188 A | 12/2000 | Saadat et al. | |
| 6,179,809 B1 | 1/2001 | Khairkhahan et al. | |
| 6,190,353 B1 | 2/2001 | Makower et al. | |
| 6,206,842 B1 | 3/2001 | Tu et al. | |
| 6,210,356 B1 | 4/2001 | Anderson et al. | |
| 6,217,543 B1 | 4/2001 | Anis et al. | |
| 6,231,546 B1 | 5/2001 | Milo et al. | |
| 6,231,587 B1 | 5/2001 | Makower | |
| 6,235,007 B1 | 5/2001 | Divino, Jr. et al. | |
| 6,241,692 B1 | 6/2001 | Tu et al. | |
| 6,241,703 B1 * | 6/2001 | Levin et al. | 604/22 |
| 6,277,084 B1 | 8/2001 | Abele et al. | |
| 6,283,983 B1 | 9/2001 | Makower et al. | |
| 6,287,271 B1 | 9/2001 | Dubrul et al. | |
| 6,287,285 B1 | 9/2001 | Michal et al. | |
| 6,287,317 B1 | 9/2001 | Makower et al. | |
| 6,296,620 B1 | 10/2001 | Gesswein et al. | |
| 6,302,875 B1 | 10/2001 | Makower et al. | |
| 6,315,741 B1 | 11/2001 | Martin et al. | |

| | | |
|---|---|---|
| 6,379,378 B1 | 4/2002 | Werneth et al. |
| 6,387,109 B1 | 5/2002 | Davison et al. |
| 6,394,956 B1 | 5/2002 | Chandrasekaran et al. |
| 6,398,736 B1 | 6/2002 | Seward |
| 6,416,533 B1 | 7/2002 | Gobin et al. |
| 6,423,026 B1 | 7/2002 | Gesswein et al. |
| 6,433,464 B2 | 8/2002 | Jones |
| 6,450,975 B1 | 9/2002 | Brennan et al. |
| 6,454,757 B1 | 9/2002 | Nita et al. |
| 6,454,997 B1 | 9/2002 | Divino, Jr. et al. |
| 6,491,707 B2 | 12/2002 | Makower |
| 6,494,891 B1 | 12/2002 | Cornish et al. |
| 6,508,781 B1 | 1/2003 | Brennan et al. |
| 6,508,784 B1 | 1/2003 | Shu |
| 6,511,458 B2 | 1/2003 | Milo et al. |
| 6,524,251 B2 | 2/2003 | Rabiner et al. |
| 6,544,215 B1 | 4/2003 | Bencini et al. |
| 6,547,754 B1 | 4/2003 | Evans et al. |
| 6,551,337 B1 | 4/2003 | Rabiner et al. |
| 6,554,846 B2 | 4/2003 | Hamilton et al. |
| 6,558,502 B2 | 5/2003 | Divino, Jr. et al. |
| 6,562,031 B2 | 5/2003 | Chandrasekaran et al. |
| 6,589,253 B1 | 7/2003 | Cornish et al. |
| 6,596,235 B2 | 7/2003 | Divino, Jr. et al. |
| 6,623,448 B2 * | 9/2003 | Slater .................. 604/95.01 |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,750 B2 | 3/2004 | Yock |
| 6,719,725 B2 | 4/2004 | Milo et al. |
| 6,733,451 B2 | 5/2004 | Rabiner et al. |
| 6,761,698 B2 | 7/2004 | Shibata et al. |
| 6,855,123 B2 | 2/2005 | Nita |
| 6,936,025 B1 | 8/2005 | Evans et al. |
| 6,936,056 B2 | 8/2005 | Nash et al. |
| 6,942,677 B2 | 9/2005 | Nita et al. |
| 7,004,173 B2 | 2/2006 | Sparks et al. |
| 7,056,294 B2 | 6/2006 | Khairkhahan et al. |
| 7,131,983 B2 | 11/2006 | Murakami |
| 7,137,963 B2 | 11/2006 | Nita et al. |
| 7,220,233 B2 | 5/2007 | Nita et al. |
| 7,335,180 B2 | 2/2008 | Nita et al. |
| 7,384,407 B2 | 6/2008 | Rodriguez et al. |
| 7,494,468 B2 | 2/2009 | Rabiner et al. |
| 7,503,895 B2 | 3/2009 | Rabiner et al. |
| 7,604,608 B2 | 10/2009 | Nita et al. |
| 2003/0009153 A1 | 1/2003 | Brisken et al. |
| 2003/0036705 A1 | 2/2003 | Hare et al. |
| 2003/0199817 A1 | 10/2003 | Thompson et al. |
| 2008/0287804 A1 | 11/2008 | Nita |

FOREIGN PATENT DOCUMENTS

| | | |
|---|---|---|
| DE | 2438648 A1 | 8/1974 |
| DE | 3821836 A1 | 6/1988 |
| DE | 4042435 | 8/1991 |
| EP | 0005719 | 12/1979 |
| EP | 0316789 B1 | 11/1988 |
| EP | 0376562 | 7/1990 |
| EP | 0379156 | 7/1990 |
| EP | 0394583 | 10/1990 |
| EP | 0443256 | 8/1991 |
| EP | 0541249 | 5/1993 |
| EP | 0820728 | 1/1998 |
| GB | 1106957 | 3/1968 |
| JP | 01099547 | 4/1989 |
| JP | U03067608 | 7/1991 |
| JP | 2006086822 | 3/1994 |
| JP | 2007116260 | 5/1995 |
| JP | 10216140 | 8/1998 |
| JP | 2001104356 | 4/2001 |
| JP | 2001321388 | 11/2001 |
| JP | 2002186627 | 7/2002 |
| WO | WO 8705739 A1 * | 9/1987 |
| WO | WO 89/06515 A1 | 7/1989 |
| WO | WO 90/01300 A1 | 2/1990 |
| WO | WO9004362 | 5/1990 |
| WO | WO9107917 | 6/1991 |
| WO | WO9211815 | 7/1992 |
| WO | WO9308750 | 5/1993 |
| WO | WO9316646 | 9/1993 |
| WO | WO9412140 | 6/1994 |
| WO | WO9414382 | 7/1994 |
| WO | WO9508954 | 4/1995 |
| WO | WO9509571 | 4/1995 |
| WO | WO9635469 | 11/1996 |
| WO | WO9745078 | 12/1997 |
| WO | WO9925412 | 5/1999 |
| WO | WO0053341 A1 | 9/2000 |
| WO | WO2004012609 | 2/2004 |
| WO | WO 2004/112888 A2 | 12/2004 |

OTHER PUBLICATIONS

Calhoun et al., "Electron-beam systems for medical device sterilization" downloaded from web on Oct. 8, 2002 <http://www.devicelink.com/mpb/archive/97/07/002.html> 7 pages total.

"E-Beam Theory" RDI-IBA Technology Group, downloaded from web on Oct. 8, 2002 <http://www.e-beam-rdi/EbeamTheory.htm> 2 pages total.

"Irradiation, biological, and other technologies: E-beam, biological, and sharps treatment systems" Chapter 9, Irradiation, Biological, and Other Technologies pp. 69-74.

"What is electron beam curing?" downloaded from web on Nov. 14, 2002 <http://www.mis.omi.gov/researchgroups/composites/new%20orccmt%020pages/pages/ebwha> 4 pages total.

* cited by examiner

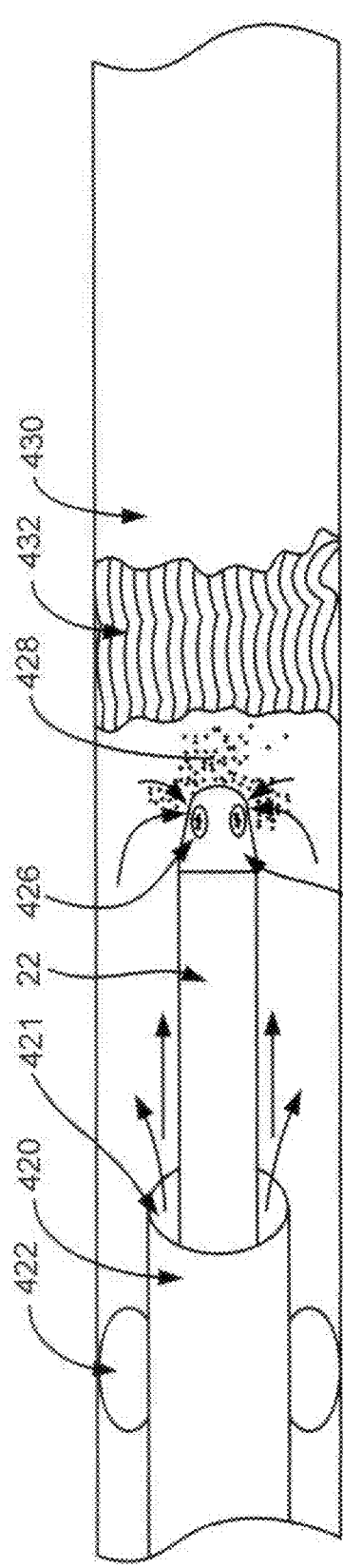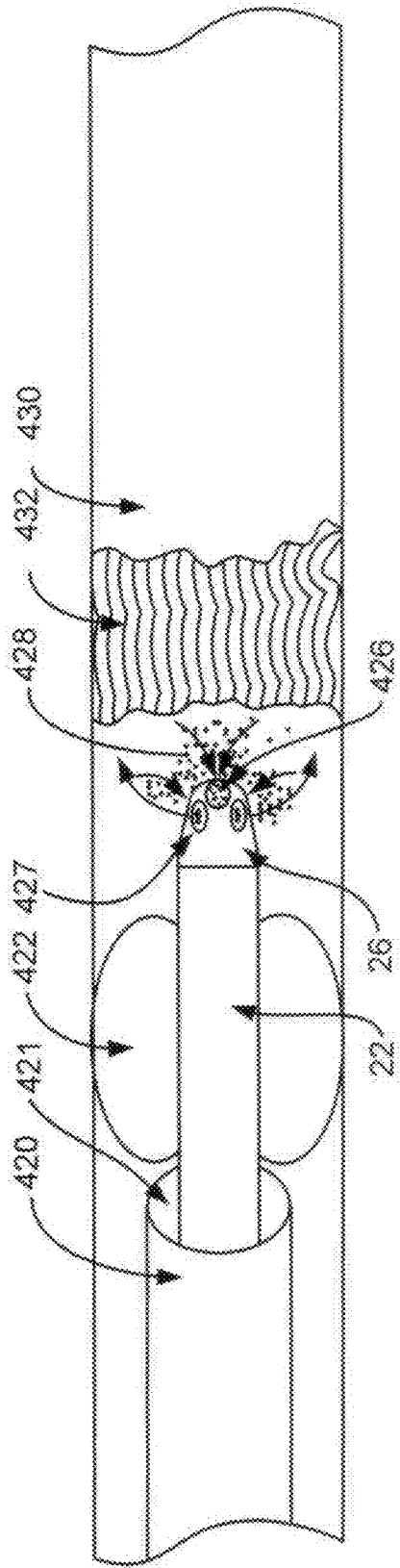

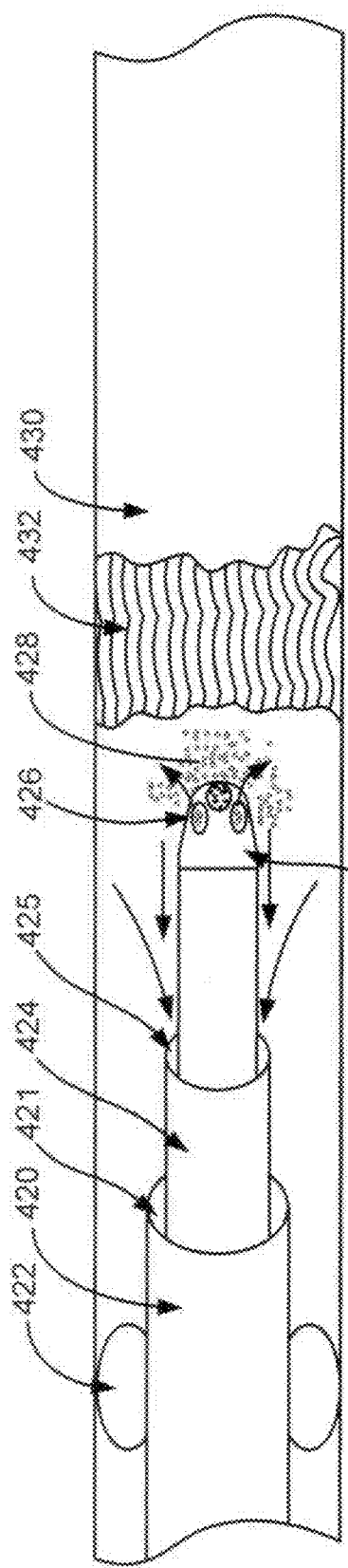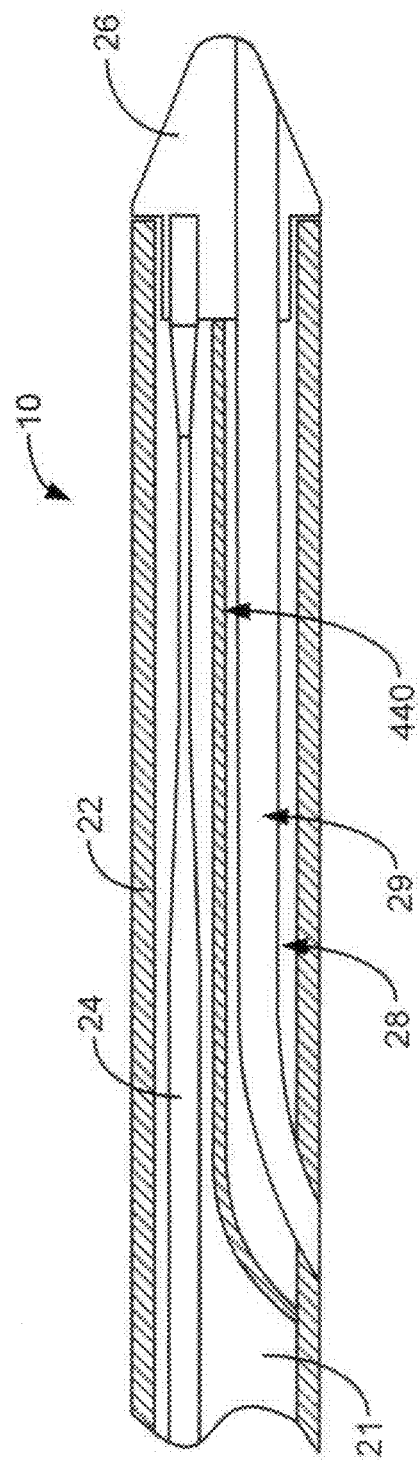

METHOD OF MANUFACTURING AN ULTRASOUND TRANSMISSION MEMBER FOR USE IN AN ULTRASOUND CATHETER DEVICE

CROSS-REFERENCE TO RELATED APPLICATIONS

The instant application is a divisional of U.S. patent application Ser. No. 10/410,617, filed Apr. 8, 2003 now U.S. Pat. No. 7,220,233, entitled "Improved Ultrasound Catheter Devices and Methods,", the full disclosure of which is incorporated herein by reference. This application is also related to the following pending U.S. Patent Applications, the full disclosures of which are all hereby incorporated by reference: application Ser. No. 10/229,371, filed Aug. 26, 2002, entitled "Ultrasound Catheter for Disrupting Blood Vessel Obstructions,"; application Ser. No. 10/345,078, filed Jan. 14, 2003, entitled "Ultrasound Catheter and Methods for Making and Using Same,"; and Ser. No. 10/375,903, filed Feb. 26, 2003, entitled "Ultrasound Catheter Apparatus,".

BACKGROUND OF THE INVENTION

The present invention relates generally to medical devices and methods. More specifically, the present invention relates to ultrasound catheter devices and methods for treating occlusive intravascular lesions.

Catheters employing various types of ultrasound transmitting members have been successfully used to ablate or otherwise disrupt obstructions in blood vessels. Specifically, ablation of atherosclerotic plaque or thromboembolic obstructions from peripheral blood vessels such as the femoral arteries has been particularly successful. Various ultrasonic catheter devices have been developed for use in ablating or otherwise removing obstructive material from blood vessels. For example, U.S. Pat. Nos. 5,267,954 and 5,380,274, issued to an inventor of the present invention and hereby incorporated by reference, describe ultrasound catheter devices for removing occlusions. Other examples of ultrasonic ablation devices for removing obstructions from blood vessels include those described in U.S. Pat. No. 3,433,226 (Boyd), U.S. Pat. No. 3,823,717 (Pohlman, et al.), U.S. Pat. No. 4,808,153 (Parisi), U.S. Pat. No. 4,936,281 (Stasz), U.S. Pat. No. 3,565,062 (Kuris), U.S. Pat. No. 4,924,863 (Sterzer), U.S. Pat. No. 4,870,953 (Don Michael, et al), and U.S. Pat. No. 4,920,954 (Alliger, et al.), as well as other patent publications W087-05739 (Cooper), W089-06515 (Bernstein, et al.), W090-0130 (Sonic Needle Corp.), EP, EP316789 (Don Michael, et al.), DE3,821,836 (Schubert) and DE2438648 (Pohlman). While many ultrasound catheters have been developed, however, improvements are still being pursued.

Typically, an ultrasonic catheter system for ablating occlusive material includes three basic components: an ultrasound generator, an ultrasound transducer, and an ultrasound catheter. The generator converts line power into a high frequency current that is delivered to the transducer. The transducer contains piezoelectric crystals which, when excited by the high frequency current, expand and contract at high frequency. These small, high-frequency expansions and contractions have both longitudinal and transverse components (relative to an axis of the transducer and the catheter), which are amplified by the transducer horn into vibrational energy. The vibrations are then transmitted from the transducer through the ultrasound catheter via an ultrasound transmission member (or wire) running longitudinally through the catheter. The transmission member transmits the vibrational energy to the distal end of the catheter where the energy is used to ablate or otherwise disrupt a vascular obstruction.

To effectively reach various sites for treatment of intravascular occlusions, ultrasound catheters of the type described above typically have lengths of about 150 cm or longer. To permit the advancement of such ultrasound catheters through small and/or tortuous blood vessels such as the aortic arch, coronary vessels, and peripheral vasculature of the lower extremities, the catheters (and their respective ultrasound transmission wires) must typically be sufficiently small and flexible. Due to attenuation of ultrasound energy along the long, thin, ultrasound transmission wire, a sufficient amount of vibrational energy must be applied at the proximal end of the wire to provide a desired amount of energy at the distal end.

An ultrasound transmission wire is usually coupled at its proximal end with the transducer by means of a sonic connector. The sonic connector typically has a significantly larger diameter than that of the ultrasound transmission member, the difference in diameters helping to amplify the vibrational energy being transmitted from the transducer to the transmission wire. Several different means have typically been used for connecting the ultrasound transmission wire with the transducer via the sonic connector, such as complementary threads, pressure fitting and the like. One shortcoming of currently available devices is that they may allow the transmission wire to rotate independently from the catheter body. In these devices, it is not possible to rotate the ultrasound transmission wire by rotating, for example, a proximal handle or sonic connector assembly, since the transmission wire rotates freely and independently of the catheter body and such a proximal assembly.

Another potential drawback of currently available devices is that they often to not include optimal means for removing particles that are broken up or dislodged by the catheter. Yet another possible shortcoming is that many ultrasound catheter devices include a distal tip, as mentioned above, but do not have means for preventing the distal tip from migrating from the device into the patient's body if the tip breaks. Similarly, most ultrasound transmission members include multiple components for transmitting vibrational energy, which causes stresses at the connection points of the multiple components during use and potential breakage of the ultrasound transmission wire or other components. Also, ultrasound transmission wires are often exposed to increased amounts of stress due to one or more bends in patient vasculature, causing increased wear and tear on the transmission wire.

Therefore, a need exists for improved ultrasound catheter devices and methods that provide ablation or disruption of vascular occlusions. Ideally, such ultrasound catheters would include means for reducing or eliminating rotational motion of the ultrasound transmission wire relative to the catheter body. It would also be advantageous to have ultrasound catheters which included means for removing particles, preventing distal tip and ultrasound transmission wire migration, preventing stress at component connection points and/or preventing stress at bends in the catheter. Such catheter devices would ideally be sufficiently thin and flexible to be advanced through narrow, tortuous vasculature, such as the coronary vasculature, while also being configured to enhance the usable life of the ultrasound transmission wire. At least some of these objectives will be met by the present invention.

BRIEF SUMMARY OF THE INVENTION

Ultrasound catheter devices and methods provide enhanced disruption of blood vessel obstructions. Generally, ultrasound catheters include an elongate flexible catheter body with one or more lumens, an ultrasound transmission member extending longitudinally through the catheter body lumen and a distal head coupled with the transmission member and positioned adjacent the distal end of the catheter body for disrupting occlusions. Improved features of ultrasound catheters include prevention of independent rotation of the ultrasound transmission member, a safety anchor for the distal head, a one-piece transmission member/distal head and the like.

In one aspect of the invention, an ultrasound catheter for disrupting occlusions in blood vessels comprises: an elongate flexible catheter body having a proximal end, a distal end and at least one lumen; an ultrasound transmission member extending longitudinally through the lumen of the catheter body and having a proximal end and a distal end; a distal head coupled with the distal end of the ultrasound transmission member and disposed adjacent the distal end of the catheter body; a sonic connector coupled with the proximal end of the ultrasound transmission member for coupling the ultrasound transmission member with an ultrasound transducer device; and a connector housing coupled with the proximal end of the catheter body for housing the sonic connector and a proximal portion of the ultrasound transmission wire and for preventing the ultrasound transmission member from rotating relative to the catheter body.

In some embodiments, the connector housing comprises a sonic connector cavity for holding the sonic connector to prevent it from rotating relative to the connector housing. Also in some embodiments, the ultrasound transducer device includes an ultrasound transducer housing having a proximal end and a distal end. In such embodiments, the connector housing may optionally be coupled with the distal end of the ultrasound transducer housing via coupling means allowing for manual coupling without using coupling tools. In one embodiment, the connector housing is coupled with the distal end of the ultrasound transducer housing via complementary threads on the two housings. Alternatively, the connector housing may be coupled with the distal end of the ultrasound transducer housing via pressure fitting. In some of these embodiments, the ultrasound transducer housing further comprises at least one protrusion on its distal end and a slidable collar for fitting over the at least one protrusion to press a portion of the distal end of the ultrasound transducer housing against the connector housing, thereby further securing the ultrasound transducer housing to the connector housing.

In another aspect, an ultrasound catheter for disrupting occlusions in blood vessels comprises: an elongate flexible catheter body having a proximal end, a distal end and at least one lumen; an ultrasound transmission member extending longitudinally through the lumen of the catheter body and having a proximal end and a distal end; a distal head coupled with the distal end of the ultrasound transmission member and disposed adjacent the distal end of the catheter body; a sonic connector coupled with the proximal end of the ultrasound transmission member for coupling the ultrasound transmission member with an ultrasound transducer device; and a rotation control member coupled with the proximal end of the catheter body for preventing the ultrasound transmission member from rotating relative to the catheter body. Optionally, the rotation control member may comprise a connector housing for housing the sonic connector and a proximal portion of the ultrasound transmission member. In some of such embodiments, the connector housing may comprise a sonic connector cavity for holding the sonic connector to prevent it from rotating relative to the connector housing. Also in some embodiments, the ultrasound transducer device includes an ultrasound transducer housing having a proximal end and a distal end. Again, the connector housing may be coupled, in some embodiments, with the distal end of the ultrasound transducer housing via coupling means allowing for manual coupling without using coupling tools. Such coupling may be by complementary threads on the two housings, pressure fitting or the like. In some embodiments, the ultrasound transducer housing further comprises at least one protrusion on its distal end and a slideable collar for fitting over the at least one protrusion to press a portion of the distal end of the ultrasound transducer housing against the connector housing, thereby further securing the ultrasound transducer housing to the connector housing.

In yet another aspect, an ultrasound catheter for disrupting occlusions in blood vessels comprises: an elongate flexible catheter body having a proximal end, a distal end and at least one lumen; an ultrasound transmission member extending longitudinally through the lumen of the catheter body and having a proximal end and a distal end; a distal head coupled with the distal end of the ultrasound transmission member and disposed adjacent the distal end of the catheter body; a sonic connector coupled with the proximal end of the ultrasound transmission member for coupling the ultrasound transmission member with an ultrasound transducer device; and means for coupling the sonic connector with the ultrasound transducer device while preventing the ultrasound transmission member from rotating relative to the catheter body. In some embodiments, the means for coupling comprises a housing for securing the sonic connector to prevent it from rotating relative to the housing.

In another aspect, an ultrasound catheter system for disrupting occlusions in blood vessels comprises: an elongate flexible catheter body having a proximal end, a distal end and at least one lumen; an ultrasound transmission member extending longitudinally through the lumen of the catheter body and having a proximal end and a distal end; a distal head coupled with the distal end of the ultrasound transmission member and disposed adjacent the distal end of the catheter body; a sonic connector coupled with the proximal end of the ultrasound transmission member; a connector housing having a proximal end and a distal end, the distal end coupled with the proximal end of the catheter body, for housing the sonic connector and a proximal portion of the ultrasound transmission wire and for preventing the ultrasound transmission member from rotating relative to the catheter body; and an ultrasound transducer device removably couplable with the sonic connector and the proximal end of the connector housing.

In some embodiments, the ultrasound transducer device includes an ultrasound transducer housing comprising at least one protrusion on a distal end of the ultrasound transducer housing and a slideable collar for fitting over the at least one protrusion to press a portion of the distal end of the ultrasound transducer housing against the connector housing, thereby further securing the ultrasound transducer housing to the connector housing. In some embodiments, the at least one protrusion comprises a first ring member at least partially encircling a portion of the ultrasound transducer housing. Sometimes the first ring member may include at least one longitudinal slot which narrows when the slideable collar is fitted over the first ring member to reduce an inner diameter of the first ring member. In some embodiments, the collar comprises a second ring member with an inner diameter to fit over at least part of the first ring member. In many embodiments, the slideable collar is slideable between an uncoupled position in which it does not contact the at least one protrusion and a coupled position in which it fits over the at least one protrusion. In some of these embodiments, the slideable collar does not overlap the connector housing when the collar is disposed in the coupled position or the uncoupled position.

In yet another aspect, an ultrasound catheter for disrupting occlusions in blood vessels comprises: an elongate flexible catheter body having a proximal end, a distal end and at least one lumen; an ultrasound transmission member extending longitudinally through the lumen of the catheter body and having a proximal end and a distal end; a distal head coupled with the distal end of the ultrasound transmission member and disposed adjacent the distal end of the catheter body; and at least one anchor member for anchoring the distal head to at least a part of the ultrasound catheter. In some embodiments, the at least one anchor member is coupled with the distal head and the catheter body. In some embodiments, the at least one anchor member is coupled with the catheter body closer to the distal end of the body than the proximal end of the body. Alternatively, the at least one anchor member may be coupled with the catheter body closer to the proximal end of the body than the distal end of the body. In other embodiments, the at least one anchor member is coupled with the distal head and a guidewire tube, the guidewire tube disposed within the catheter body and coupled with the catheter body. In yet other embodiments, the at least one anchor member comprises a guidewire tube disposed within the catheter body and coupled with the catheter body. In some embodiments, the at least one anchor member is coupled with at least one of the distal head and the catheter body by means selected from the group consisting of bonding, welding, fusing, tying and heat shrinking. In some embodiments, the at least one anchor member comprises at least one of a metal and a polymer.

In another aspect, an ultrasound catheter for disrupting occlusions in blood vessels, comprises: an elongate flexible catheter body having a proximal end, a distal end and at least one lumen; an ultrasound transmission member extending longitudinally through the lumen of the catheter body and having a proximal end, a distal end and a distal head, wherein the distal head and the rest of the ultrasound transmission member are manufactured from one piece of material; and a sonic connector coupled with the proximal end of the ultrasound transmission member for coupling the ultrasound transmission member with an ultrasound transducer device. In some embodiments, the ultrasound transmission member comprises at least one material having superelastic properties. Also in some embodiments, the distal head of the ultrasound transmission member comprises at least one longitudinal aperture. For example, the at least one longitudinal aperture may comprise at least one of an irrigation aperture and a guidewire aperture. In some embodiments, the ultrasound transmission member tapers from a larger diameter at its proximal end to a smaller diameter adjacent the distal head.

In another aspect, an ultrasound catheter for disrupting occlusions in blood vessels, includes: an elongate flexible catheter body having a proximal end, a distal end and at least one lumen; an ultrasound transmission member extending longitudinally through the lumen of the catheter body and having a proximal end and a distal end, the ultrasound transmission member comprising a metal alloy including at least two metal components and having a tensile strength of between 170,000 Psi and 250,000 Psi; and a distal head coupled with the distal end of the ultrasound transmission member and disposed adjacent the distal end of the catheter body, the distal head having an average density not to exceed 5 g/cm3. In some cases, the metal alloy comprises a superelastic alloy. For example, the superelastic alloy may be capable of elongation of between 7% and 17% in some embodiments. In one embodiment, the superelastic alloy comprises a nickel-titanium alloy having a nickel content of between 50.50 and 51.50 atomic weight. Optionally, the superelastic alloy may have a superelastic temperature range of between 10° C. and 50° C.

In still another aspect, an ultrasound catheter for disrupting occlusions in blood vessels includes: an elongate flexible catheter body having a proximal end, a distal end and at least one lumen, the catheter body comprising at least in part a polymeric material having a flexural modulus of elasticity of less than 160 Psi; an ultrasound transmission member extending longitudinally through the lumen of the catheter body and having a proximal end and a distal end; a distal head coupled with the distal end of the ultrasound transmission member and disposed adjacent the distal end of the catheter body; and a sonic connector coupled with the proximal end of the ultrasound transmission member for coupling the ultrasound transmission member with an ultrasound transducer device. In some embodiments, the polymeric material comprises a polymeric block amide. In some embodiments, the polymeric block amide has a Shore D hardness value of between about 55 and about 75. Alternatively, the polymeric block amide may have a Shore D hardness value of between about 25 and about 55. Also in some embodiments, 5% or less of the polymeric material may comprise a colorant.

In another aspect of the invention, a method of manufacturing an ultrasound transmission member for use in an ultrasound catheter device involves: providing a generally cylindrically-shaped transmission member material; shaping the material to taper the transmission member from a first, wider end toward a second, narrower end; and forming a distal head at the second, narrower end. In some cases, providing the material comprises providing a polymer having superelastic properties. Shaping the material, in some embodiments, comprises grinding the material. Forming the distal head, in some embodiments, comprises forming a bullet-shaped head. Optionally, forming the distal head may further comprise forming at least one longitudinal aperture through the head to provide for passage of at least one of a guidewire and irrigation fluid.

In another aspect, a method for disrupting an occlusion in a blood vessel includes: positioning an ultrasound catheter in the blood vessel such that a distal end of the catheter is adjacent the occlusion; transmitting ultrasound energy to an ultrasound transmission member of the ultrasound catheter to disrupt the occlusion into multiple occlusion fragments; expanding an expandable balloon coupled with the ultrasound catheter at a location proximal to the distal end of the catheter; and removing at least some of the occlusion fragments from the blood vessel via the ultrasound catheter. In some embodiments, positioning the ultrasound catheter comprises guiding the catheter using a guidewire. Optionally, the occlusion fragments may be removed through at least one aperture in a catheter body of the ultrasound catheter. In some embodiments, for example, the at least one aperture is in fluid communication with at least one irrigation lumen and the occlusion fragments are removed through the at least one aperture and the at least one irrigation lumen. Alternatively, the at least one aperture may be in fluid communication with at least one guidewire lumen and the occlusion fragments are removed through the at least one aperture and the at least one guidewire lumen. In another embodiment, the occlusion fragments are removed through a sheath disposed around a portion of the ultrasound catheter. In any such embodiments, removing the occlusion fragments may comprise applying a vacuum force to guide the fragments into at least one aperture on the ultrasound catheter. For example, applying the vacuum may comprise using at least one of a syringe and a vacuum pump.

In another aspect of the invention, a method for disrupting an occlusion in a blood vessel comprises: introducing an ultrasound catheter into the blood vessel through a guide catheter; positioning the ultrasound catheter such that a distal end of the catheter is adjacent the occlusion; transmitting ultrasound energy to an ultrasound transmission member of the ultrasound catheter to disrupt the occlusion into multiple occlusion fragments; expanding an expandable balloon coupled with the guide catheter at a location proximal to the distal end of the catheter; and removing at least some of the occlusion fragments from the blood vessel via the ultrasound catheter. Optionally, introducing and positioning the ultrasound catheter may further comprise guiding the catheter using a guidewire.

In yet another aspect, a method for disrupting an occlusion in a blood vessel involves: positioning an ultrasound catheter in the blood vessel such that a distal end of the catheter is adjacent the occlusion; introducing at least one radiopaque fluid into the blood vessel through at least one aperture in the ultrasound catheter adjacent the distal end to enhance visualization of a location of the distal end; and transmitting ultrasound energy to an ultrasound transmission member of the ultrasound catheter to disrupt the occlusion into multiple occlusion fragments. Optionally, introducing the radiopaque fluid may comprise introducing through at least one irrigation aperture in the ultrasound catheter. Alternatively, introducing the radiopaque fluid may comprise introducing through at least one guidewire aperture in the ultrasound catheter. In yet other embodiments, introducing the radiopaque fluid comprises introducing through a sheath surrounding a portion of the ultrasound catheter and forming the at least one aperture.

BRIEF DESCRIPTION OF THE DRAWINGS

FIG. 6 is a side view of an ultrasound catheter device with a balloon and apertures for irrigation and suction according to an embodiment of the present invention;

FIG. 7 is a side view of an ultrasound catheter device with a balloon and apertures for irrigation and suction according to another embodiment of the present invention;

FIG. 8 is a side view of an ultrasound catheter device with a balloon and apertures for irrigation and suction according to still another embodiment of the present invention;

FIG. 9 is a cross-sectional side view of a distal end of an ultrasound catheter device with an anchor member according to an embodiment of the present invention;

DETAILED DESCRIPTION OF THE INVENTION

Ultrasound catheter devices and methods of the present invention may generally be used for treating occlusions in blood vessels. Catheter devices generally include a catheter body, an ultrasound energy transmission member disposed within the catheter body and a distal head coupled with the energy transmission member and disposed at or near the distal end of the catheter body. The ultrasound transmission member transmits ultrasound energy from an ultrasound transducer to the distal head, causing the head to vibrate and, thus, disrupt vascular occlusions. A number of improved features of such ultrasound catheter devices are described more fully below.

Figure 1:
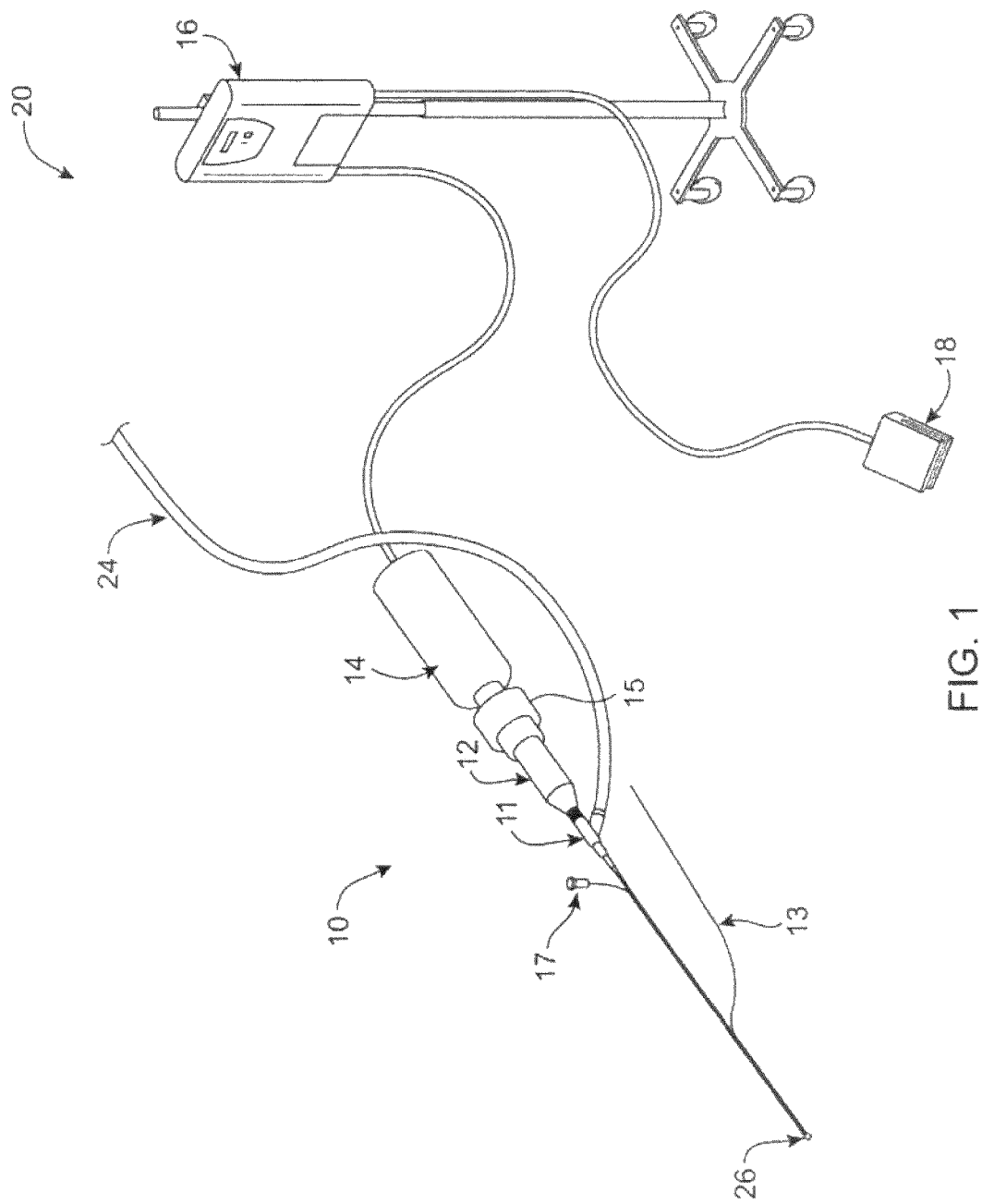
FIG. 1 is a perspective view of a system including an ultrasound catheter device and ultrasound energy source according to an embodiment of the present invention.

Referring now to FIG. 1, one embodiment of an ultrasound catheter system 20 suitably includes an ultrasound catheter device 10, including a proximal end connector 12 for coupling device 10 with an ultrasound transducer 14, and an ultrasound generator 16 coupled with transducer 14 and a foot-actuated on/off switch 18 to provide ultrasonic energy to transducer 14 and, thus, to ultrasound catheter 10. Generally, catheter 10 includes an ultrasound transmission member, or wire (not shown), for transmitting energy from the transducer 14 to a distal head 26 of catheter 10. In some embodiments, transducer 14 further includes a securing device 15 for enhancing coupling of catheter 10 to transducer 14. Components of system 20 may be coupled via any suitable means, such as connecting wires of any kind, wireless connections or the like.

In addition to proximal connector 12, ultrasound catheter device 10 may include one or more other various components, such as a Y-connector 11 or the like for providing access for irrigation, guidewire passage, suction or the like. Some embodiments of device include a rapid exchange guidewire 13, some include a proximal guidewire port 17 for over the wire guidewire deliver, and some embodiments include both. In some embodiments, Y-connector may include an irrigation port, for providing access for an irrigation tube 24. Irrigation tube 24, in some embodiments, may be used for introducing one or more fluids, applying vacuum, or both. Generally, catheter device 10 may include any suitable number of sidearms or ports for passage of a guidewire, infusing and/or withdrawing irrigation fluid, dye and/or the like, or any other suitable ports or connections. Also, ultrasound catheters 10 of the present invention may be used with any suitable proximal devices, such as any suitable ultrasound transducer 14, ultrasound generator 16, coupling device(s) and/or the like. Therefore, exemplary FIG. 1 and any following descriptions of proximal apparatus or systems for use with ultrasound catheters 10 should not be interpreted to limit the scope of the present invention as defined in the appended claims.

Figure 3:
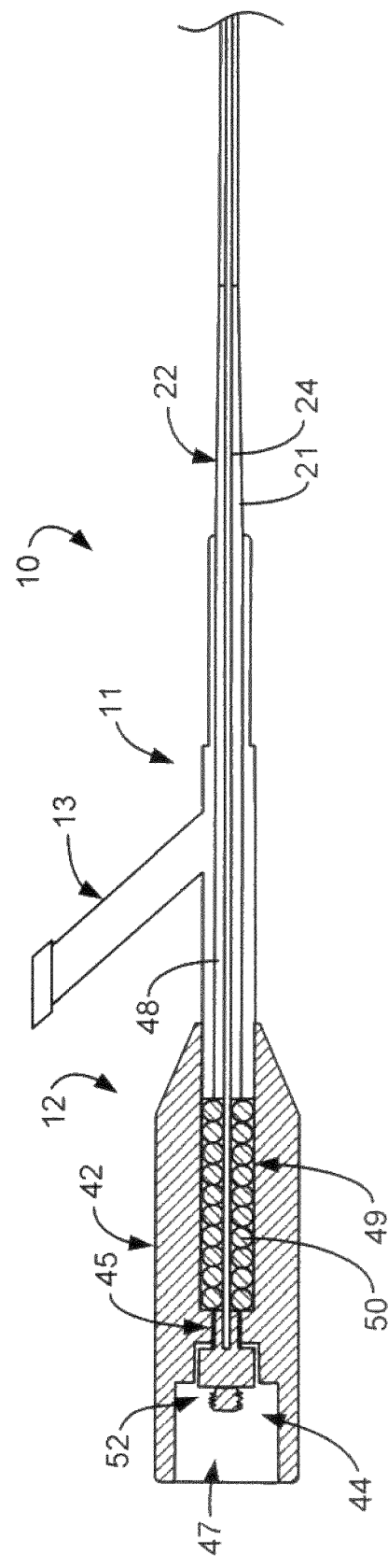
FIG. 3 is a cross-sectional side view of an ultrasound catheter device according to an embodiment of the present invention.

Referring now to FIG. 3, a cross-sectional side view of one embodiment of ultrasound catheter device 10 is shown. Generally, ultrasound catheter 10 suitably includes an elongate catheter body 22 with an ultrasound transmission member 24 disposed longitudinally through a catheter lumen 21 and ending in distal head (not shown). Catheter body 22 is generally a flexible, tubular, elongate member, having any suitable diameter and length for reaching a vascular occlusion for treatment. In one embodiment, for example, catheter body 22 preferably has an outer diameter of between about 0.5 mm and about 5.0 mm. In other embodiments, as in catheters intended for use in relatively small vessels, catheter body 22 may have an outer diameter of between about 0.25 mm and about 2.5 mm. Catheter body 22 may also have any suitable length. As discussed briefly above, for example, some ultrasound catheters have a length in the range of about 150 cm. However, any other suitable length may be used without departing from the scope of the present invention. Examples of catheter bodies similar to those which may be used in the present invention are described in U.S. Pat. Nos. 5,267,954 and 5,989,208, which were previously incorporated herein by reference.

In some embodiments, catheter body 22 is made from a polymeric material. Sometimes the polymer will have a desired amount of flexibility, such as in one embodiment where catheter body 22 is made of a polymer having a flexural modulus of less than about 160 Psi. In some embodiments, such a polymer will be one of any number of polyether block amides, although other polymers may of course be used. In some embodiments, such polyether block amides may have a Shore D hardness value ranging from about 55 to about 75, while in other embodiments they may have a Shore D hardness value ranging from about 25 to about 55. In some embodiments, the polymeric material includes up to about 5 weight percent of a colorant.

In most embodiments, ultrasound transmission member 24, wire, or wave guide extends longitudinally through catheter body lumen 21 to transmit ultrasonic energy from ultrasound transducer 14, connected to the proximal end of catheter 10, to the distal end of catheter 10. Ultrasound transmission member 24 may be formed of any material capable of effectively transmitting ultrasonic energy from ultrasound transducer 14 to the distal end of catheter body 22, including but not limited to metals such as pure titanium or aluminum, or titanium or aluminum alloys.

With continued reference to FIG. 3, one embodiment of proximal end connector 12 suitably includes a housing 42 with a hollow inner bore 44. Bore 44 may have a uniform inner diameter along its length or, alternatively, may have multiple segments, such as a proximal segment 47, a middle segment 45 and a distal segment 49, each of which may surround one or more various components of proximal end connector 12. Generally, proximal segment 47 of bore 44 is configured to allow coupling with ultrasound transducer 14 (not shown) via any suitable coupling means, such as a pressure fit, complementary threads or the like. Proximal segment 47 includes a sonic connector 52 for transmitting vibrational energy from transducer 14 to ultrasound transmission member 24. Sonic connector 52 may be held within housing 42 by any suitable means. In some embodiments, for example, a dowel pin may extend through sonic connector 52 to hold it within housing 42.

Figure 2:
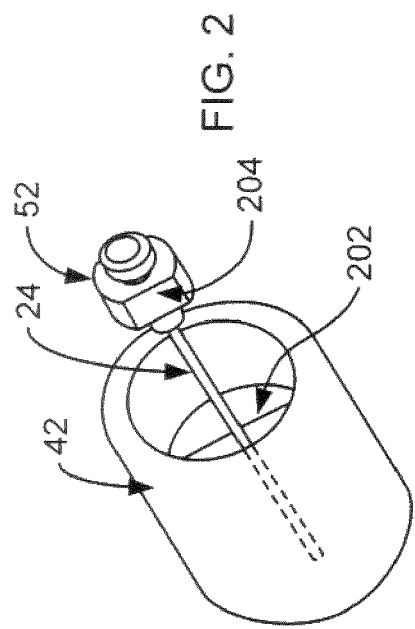
FIG. 2 is a perspective view of a proximal housing, sonic connector and ultrasound transmission member of an ultrasound catheter device according to an embodiment of the present invention.

In another embodiment, and with reference now to FIG. 2, sonic connector 52 may be secured within housing 42 by means of a cavity 202 in housing 42. Cavity 202, in some embodiments, will have a complementary shape to sonic connector 52, such that sonic connector 52 fits snugly within cavity 202 to prevent rotation of sonic connector 52 independent of housing 42. In FIG. 2, for example, sonic connector 52 has flat sides 204 which correspond with the shape of cavity 202. Any other suitable shape/configuration is contemplated. By preventing free rotation of sonic connector 52, housing 42 and cavity 202 also prevent free rotation of ultrasound transmission member 24, which is securely coupled with sonic connector 52. Conversely, if rotation of ultrasound transmission member 24 is desired, a user of device 10 can rotate housing 42, such as by rotating it in his/her hand, and this rotation of housing 42 will be transmitted to sonic connector 52 and ultrasound transmission member 24.

Returning to FIG. 3, middle segment 45 of bore 44, in some embodiments, may surround a portion of sonic connector 52, while in other embodiments, sonic connector 52 may be housed only within proximal segment 47. Sonic connector 52 is coupled with the proximal end of ultrasound transmission member 24 by any suitable means for transmitting ultrasound energy to transmission member 24 from transducer 14. Absorber members 50, such as O-rings, surround a portion of ultrasound transmission member 24 for providing absorption of transverse vibration. Absorber members 50 may be used in any number or combination and have and suitable size and configuration, depending on the desired level of vibration absorption or dampening. Alternatively or additionally, other dampening structures may be used. Thus, the invention is not limited to the combination shown in FIG. 3.

Distal segment 49 of bore 44 typically surrounds a portion of ultrasound transmission member 24 and may also contain one or more additional sets of absorber members 50. Distal segment 49 may also contain a portion of a Y-connector 11, which is coupled with the distal end of housing 42. Coupling of Y-connector 11 with the distal end of housing 42 may be accomplished via complementary threads, pressure fitting, or any other suitable means. A Y-connector lumen 48 of Y-connector 11 allows passage of ultrasound transmission member 24 and is in fluid communication with catheter body lumen 21.

Generally, pressurized fluid such as a coolant liquid may be infused through a side-arm 13 of Y-connector, through Y-connector lumen 48 and through catheter body lumen 21 so that it flows out of one or more fluid outflow apertures in distal head 26. The temperature and flow rate of such coolant liquid may be specifically controlled to maintain the temperature of ultrasound transmission member 24 at a desired temperature within its optimal working range. In particular, in embodiments of the invention wherein ultrasound transmission member 24 is formed of a metal alloy which exhibits optimal physical properties (e.g. super elasticity) within a specific range of temperatures, the temperature and flow rate of coolant liquid infused through fluid infusion side-arm 13 may be specifically controlled to maintain the temperature of ultrasound transmission member 24 within a range of temperatures at which it demonstrates its most desirable physical properties. For example, in embodiments of the invention wherein ultrasound transmission member 24 is formed of a shape memory alloy which exhibits super elasticity when in its martensite state, but which loses super elasticity as it transitions to an austenite state, it will be desirable to adjust the temperature and flow rate of the coolant liquid infused through fluid infusion side-arm 13 so as to maintain the shape memory alloy of ultrasound transmission member 24 within a temperature range at which the alloy will remain in its martensite state and will not transition to an austenite state. The temperature at which such shape memory alloys transition from a martensite state to an austenite state is known as the "martensite transition temperature" of the material. Thus, in these embodiments, the fluid infused through side-arm 13 will be at such temperature, and will be infused at such rate, as to maintain the shape memory alloy of ultrasound transmission member 24 below its martensite transition temperature.

Figure 4A:
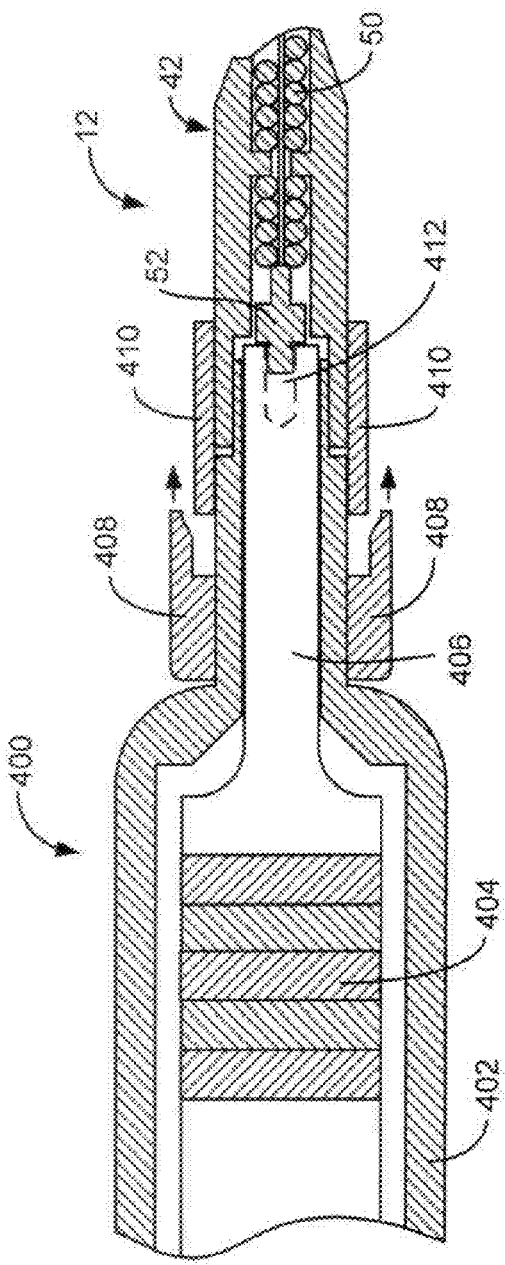
FIGS. 4A and 4B are cross-sectional side views of a proximal portion of an ultrasound catheter device coupled with a distal end of an ultrasound transducer device, showing a collar in unengaged (FIG. 4A) and engaged (FIG. 4B) positions according to an embodiment of the present invention.
Figure 4B:
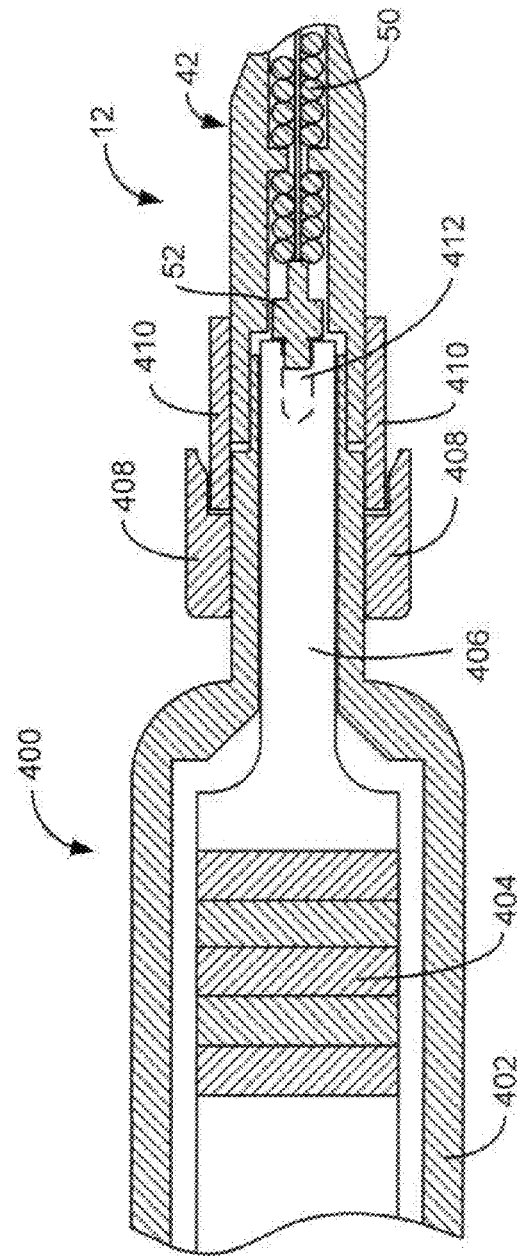

Referring now to FIGS. 4A and 4B cross-sectional side views of one embodiment of the coupling of proximal connector 12 with the distal end of a transducer device 400. Generally, transducer device will include a transducer housing 402, piezoelectric crystals 404, a transducer horn 406, and any suitable coupling means 412 for coupling transducer horn 406 with sonic connector 52. Coupling means 412 may include, for example, complementary threads, a pressure fitting configuration or the like. In some embodiments, transducer housing 402 includes a slidable collar 408 and at least one surface protrusion 410. Surface protrusion 410 generally fits over the outer surface of housing 42 of proximal connector 12. In some embodiments, as shown in FIGS. 4A and 4B, protrusion 410 may be a ring surrounding a portion of transducer housing 402, though any other configuration is contemplated. Slidable collar 408, in turn, is slidable between an unengaged position, as in FIG. 4A, and an engaged position, as in FIG. 4B. In the engaged position, slidable collar 408 fits around the outer diameter of protrusion 410 sufficiently tightly to apply pressure against protrusion 410. This pressure presses protrusion 410 against housing 42 to further secure transducer housing 402 to proximal connector 12. This further securing prevents unwanted separation of ultrasound catheter device 10 from transducer device 400. Any other suitable configurations, shapes, sizes and the like of collar 408 and protrusion 410 are contemplated.

Figure 5A:
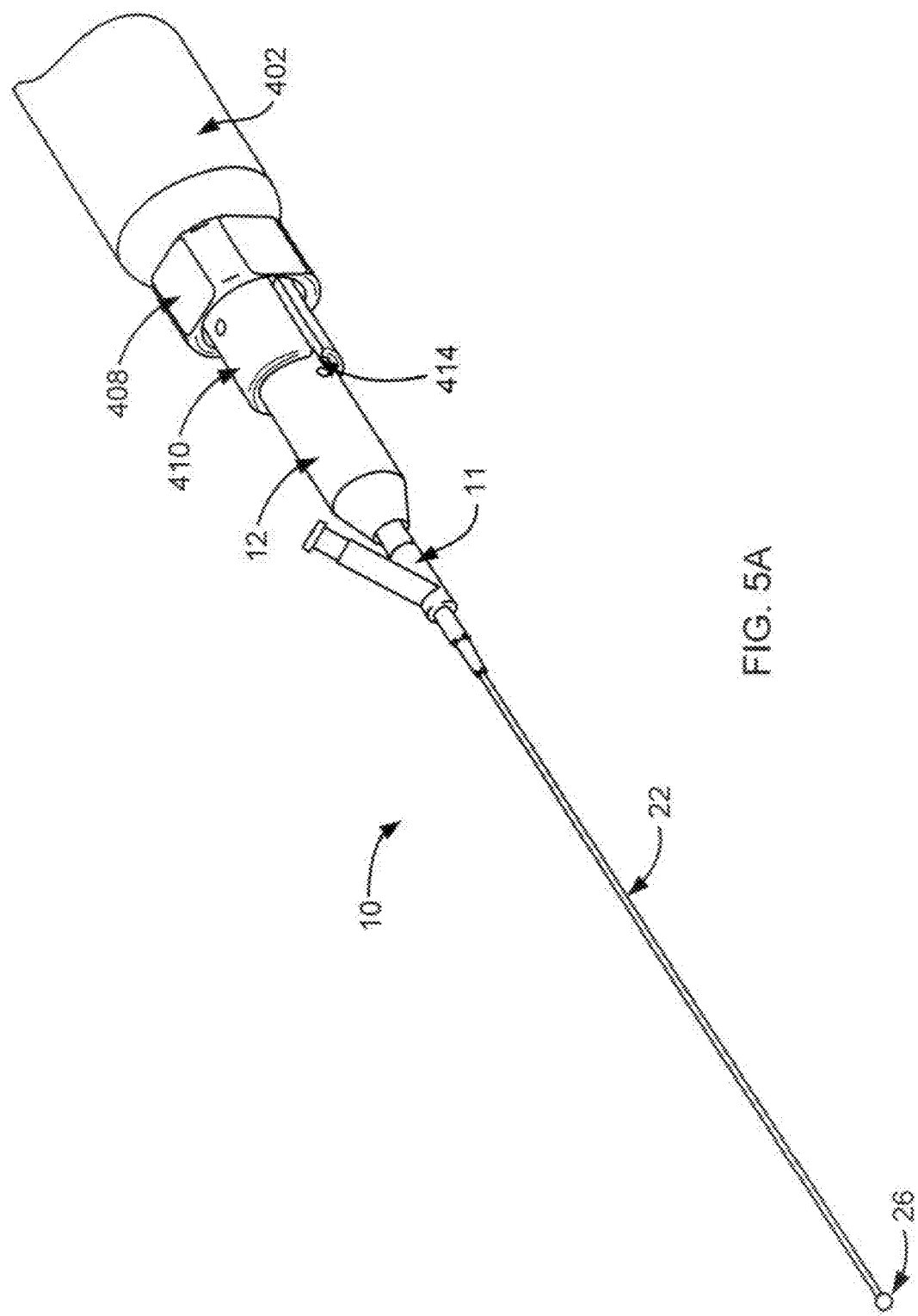
FIGS. 5A and 5B are perspective views of an ultrasound catheter device coupled with a distal end of an ultrasound transducer device, showing a collar in unengaged (FIG. 5A) and engaged (FIG. 5B) positions according to an embodiment of the present invention.
Figure 5B:
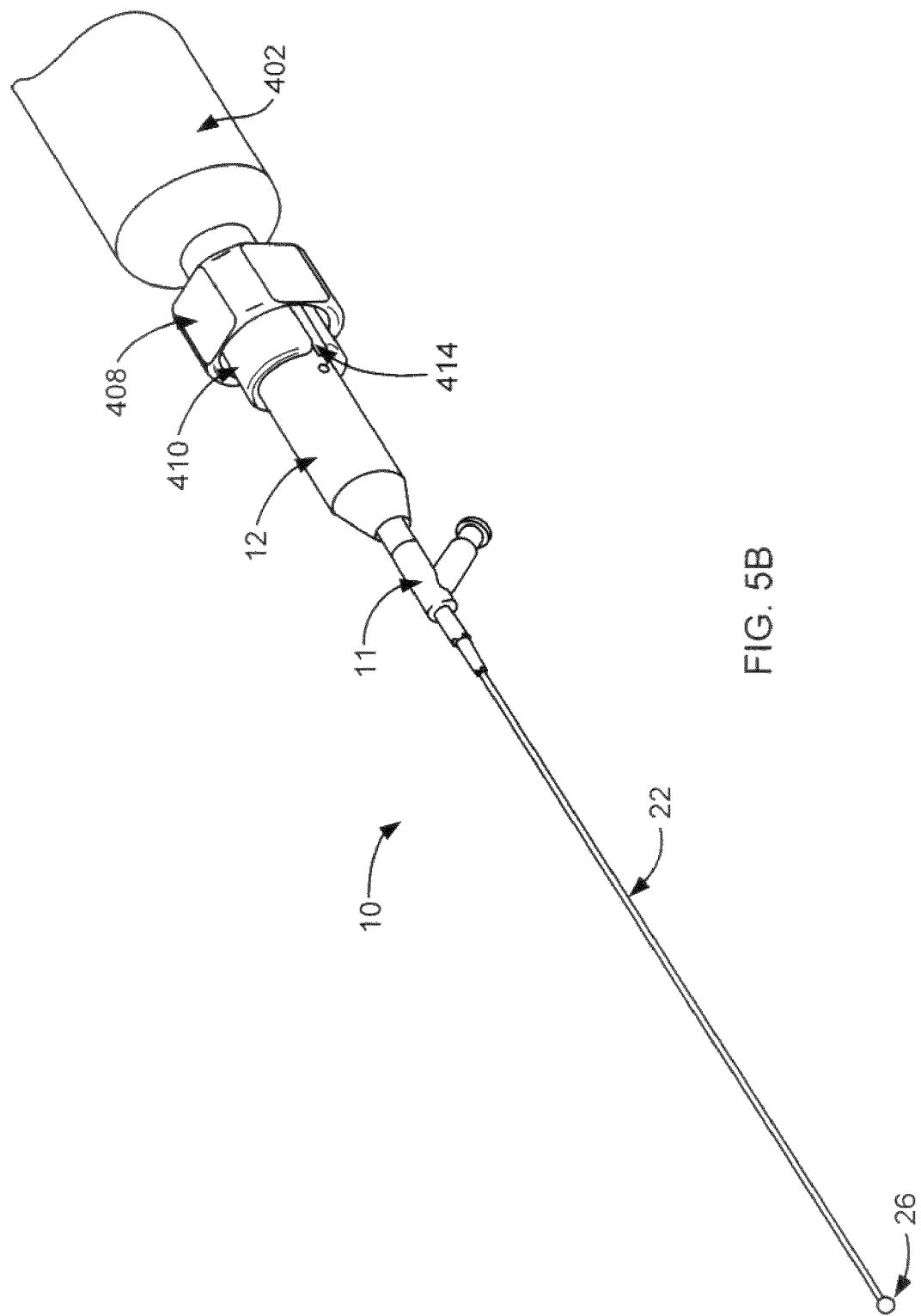

With reference now to FIGS. 5A and 5B, ultrasound catheter device 10 is shown coupled with transducer housing 402. FIG. 5A shows slidable collar 408 in its unengaged position, while FIG. 5B shows collar 408 in its engaged position. In some embodiments, protrusion 410 may be a ring making up or surrounding a portion of transducer housing 402, as mentioned above. Also in some embodiments, protrusion 410, such as a ring, may include a slot 414 or other opening, which may go through all or part of the thickness of protrusion 410. Slot 414 generally allows protrusion 410 to give or bend when collar 408 is fitted over protrusion 410, thus reducing the inner diameter of protrusion 410 to press against the outer surface of proximal connector device 12. Again, any suitable configuration for slot 414 is contemplated within the scope of the present invention. When collar 408 is engaged, as shown in FIG. 5B, transducer housing 402 or proximal connector 12 may be rotated, and ultrasound catheter device 10 (with ultrasound transmission member 24) will rotate in turn. Such rotation may be accomplished even when collar 408 is in the unengaged position (FIG. 5A), but collar 408 and protrusion 410 enhance coupling of transducer housing 402 and proximal connector 12, to provide additional control and to assure that transducer housing 402, proximal connector 12 and the rest of ultrasound catheter device 10 either rotate together or do not rotate.

Referring now to FIGS. 6-8, various embodiments of a distal end of ultrasound catheter device 10 are shown within a blood vessel 430, adjacent an occlusion 432. Various embodiments of ultrasound catheter device 10 include one or more expandable members 422, such as balloons, as well as one or more fluid apertures 426 in distal head 26. Some embodiments may also include, or may be used in conjunction with, a guide catheter 420 having a guide catheter aperture 421. In one embodiment, as shown in FIG. 6, fluid may be introduced adjacent occlusion 432 via fluid apertures 426 and/or guide catheter aperture 421. Once catheter device 10 has begun to break occlusion 432 into multiple fragments 428, fluid (either by itself or containing the fragments) may be removed from blood vessel 430 via fluid apertures 426 and/or guide catheter aperture 421. In FIG. 6, fluid is being introduced via guide catheter aperture 421 (arrows), and fluid and fragments 428 are being removed via fluid apertures 426. The opposite may also be possible. Such fluid introduction and fluid/fragment removal are enhanced in some embodiments by expanding a balloon 422 proximal to the fluid introduction/removal apertures. In the embodiment shown in FIG. 6, balloon 422 is coupled with guide catheter 420.

With reference to FIG. 7, in an alternative embodiment, balloon 422 is coupled with catheter body 22 rather than guide catheter 420. In this embodiment, fluid may be introduced by one or more fluid apertures 427 and fluid and fragments 428 may be removed via one or more other fluid apertures 426. Generally, any suitable combination of fluid apertures 426, 427 for infusion of fluids and/or aspiration of fluids and/or particles may be used. In yet another embodiment, and with reference now to FIG. 8, ultrasound catheter device 10 may include a sheath 424 around its outer circumference, the sheath forming a sheath aperture 425. Sheath aperture 425 may then be used for fluid introduction and/or removal of fluid/fragments 428. In FIG. 8, for example, fluid is shown exiting fluid apertures 426 and entering sheath aperture 425 (arrows). Virtually any suitable combination of apertures and expandable members is contemplated by the present invention. The use of apertures and expandable members generally enhances operation of ultrasound catheter device in breaking down occlusions and removing occlusion fragments harmlessly from the patient.

Figure 10:
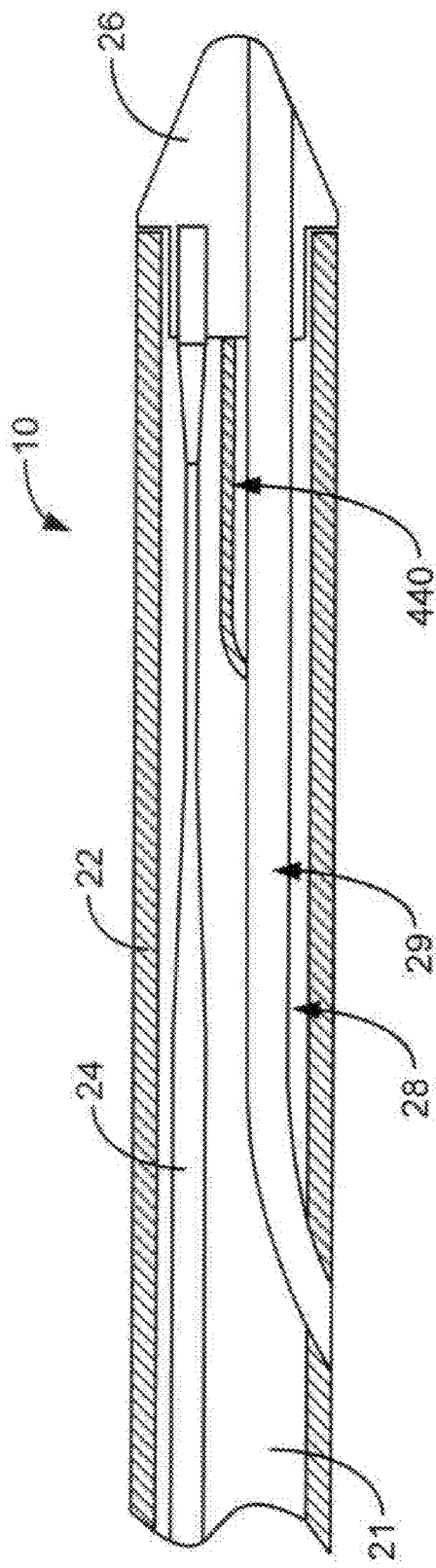
FIG. 10 is a cross-sectional side view of a distal end of an ultrasound catheter device with an anchor member according to another embodiment of the present invention.
Figure 11:
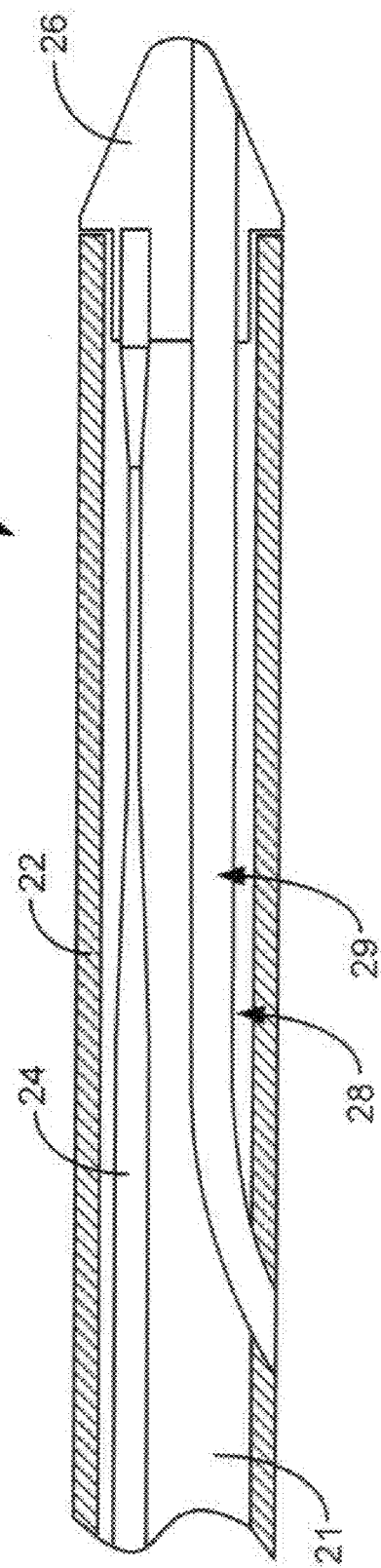
FIG. 11 is a cross-sectional side view of a distal end of an ultrasound catheter device with an anchor member according to still another embodiment of the present invention.

With reference now to FIGS. 9-11, various embodiments of the distal end of ultrasound catheter device 10 are shown in cross-sectional side view suitably includes an elongate catheter body 22 with at least one hollow catheter body lumen 21. In FIGS. 9-11, catheter body 22 is shown having one lumen 21, but it may have any number of lumens in various embodiments. Disposed longitudinally within catheter body lumen 21 are an ultrasound transmission member 24 and a hollow guidewire tube 28 forming a guidewire lumen 29. Coupled with the distal ends of ultrasound transmission member 24 and guidewire tube 28 is a distal head 26, positioned adjacent the distal end of catheter body 22.

Generally, the various coupled components described above may be coupled by any suitable means, such as adhesives, complementary threaded members, pressure fittings, and the like. For example, distal head 26 may be coupled with ultrasound transmission member 24 and guidewire tube 28 with any suitable adhesive substance or via welding, bonding or the like. Adhesives used to attach guide wire tube 28, distal head 26 and/or catheter body 22 may include, but are not limited to cyanoacrylate (eg. Loctite™, Loctite Corp., Ontario, CANADA or Dron Alpha™, Borden, Inc., Columbus, Ohio) or polyurethane (e.g. Dymax™, Dymax Engineering Adhesive, Torrington, Conn.) adhesives. In some embodiments, guidewire tube 28 may also be coupled with catheter body 22 by adhesive, welding or other means. Some embodiments may also include one or more anchoring members for further securing distal head 26 to the ultrasound catheter device 10 and to help ensure that distal head 26 does not break free of catheter device 10.

For example, referring to FIG. 9, in one embodiment an anchoring member 440 may be connected at one end to distal head 26 and at the other end to catheter body 22. Again, any connection means may be used, such as but not limited to adhesives, welding, bonding and/or the like. Furthermore, anchoring member 440 may be connected to distal head 26 and catheter body 22 at any suitable locations. Another embodiment is shown in FIG. 10, in which anchoring member 440 is coupled with distal head 26 and guidewire tube 28. This connection may provide similar safety and prevention of distal head 26 migration. Finally, in some embodiments, as shown in FIG. 11, guidewire tube 28 itself acts as an anchor, and a separate anchoring member is not used. Any suitable configuration and combination is contemplated by the scope of the present invention.

Figure 12A:
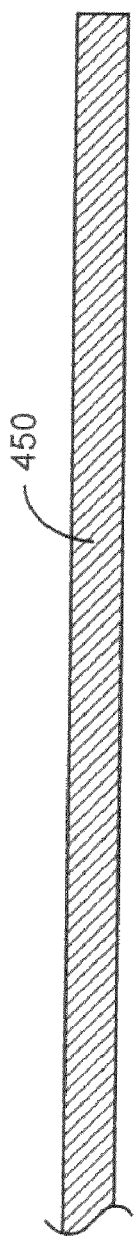
FIGS. 12A-12C illustrate a method of manufacturing an ultrasound transmission member for use in an ultrasound catheter device according to an embodiment of the present invention.
Figure 12B:
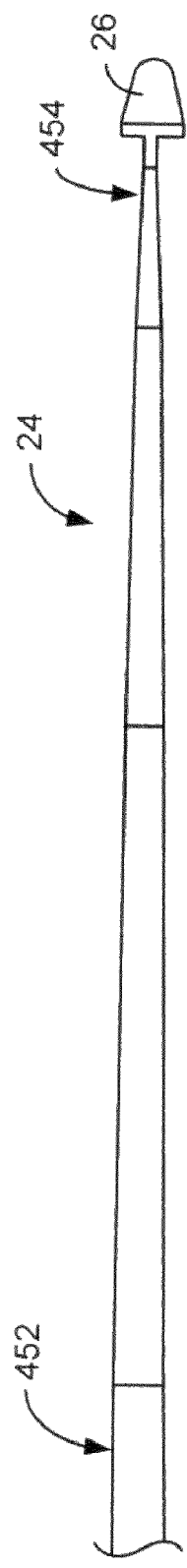
Figure 12C:
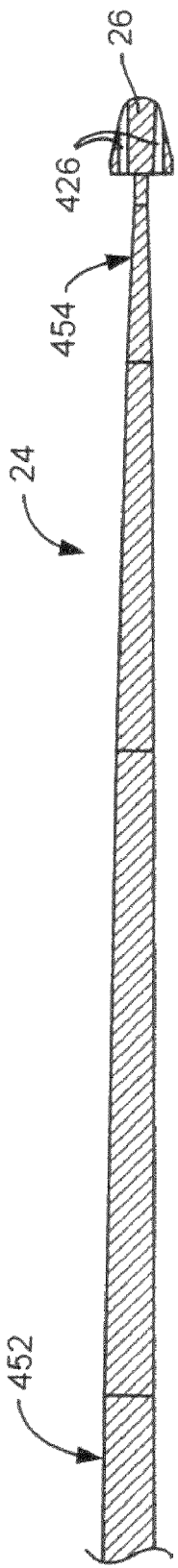

Finally, and with reference now to FIGS. 12A-12C, one embodiment of an ultrasound transmission member 24 and a method for making same is shown. In this embodiment, ultrasound transmission member 24 is made from a unitary piece of precursor material 450 and includes distal head 26. Thus there is no separate distal head piece that is attached to ultrasound transmission member 24—instead it is all one piece. Generally, ultrasound transmission member 24 may be formed of any material 450 capable of effectively transmitting ultrasonic energy from ultrasound transducer 14 to the distal end of catheter body 22, including but not limited to metals such as titanium and nickel alloys.

In accordance with one aspect of the invention, all or a portion of ultrasound transmission member 24 may be formed of one or more materials 450 which exhibit superelastic properties. Such material(s) 450 should preferably exhibit superelasticity consistently within the range of temperatures normally encountered by ultrasound transmission member 24 during operation of ultrasound catheter apparatus 10. For example, in some embodiments, material 450 is an alloy having a tensile strength of between about 170,000 Psi and about 250,000 Psi. In some embodiments, the alloy exhibits elongation of between about 7% and about 17%. For example, in some embodiments the alloy is a nickel-titanium alloy having nickel content of between about 50.50 and about 51.50 atomic weight.

Use of superelastic metal alloys in ultrasound transmission members is described in U.S. Pat. No. 5,267,954, previously incorporated by reference. Examples of superelastic metal alloys which may be used are described in detail in U.S. Pat. No. 4,665,906 (Jervis); U.S. Pat. No. 4,565,589 (Harrison); U.S. Pat. No. 4,505,767 (Quin); and U.S. Pat. No. 4,337,090 (Harrison), the entire disclosures of which are hereby incorporated by reference insofar as they describe the compositions, properties, chemistries and behavior of specific metal alloys which are superelastic within the temperature range at which ultrasound transmission member 24 of the present invention operates, any and all of which superelastic metal alloys may be used to form ultrasound transmission member 24 of the present invention. In some embodiments, for example, the alloy exhibits a superelastic temperature range of about 10 degrees Celsius to about 50 degrees Celsius.

In many embodiments, ultrasound transmission member 24 includes a wider region 452 toward its proximal end and one or more tapered regions 454 towards its distal end. Tapered region 454 decreases the distal rigidity of ultrasound transmission member 24, thus amplifying ultrasound energy transmitted along ultrasound transmission member 24 to distal head 26. Distal head 26 may have any suitable configuration, shape, and size suitable for ablating or otherwise disrupting occlusions. For example, distal head 26 may have a shape that is bulbous, conical, cylindrical, circular, rectangular or the like. Similarly, distal head 26 may have dimensions which allow it to fit wholly or partially within the distal end of catheter body lumen 21 or may, alternatively, be disposed completely outside catheter body lumen 21. Thus, the configuration of distal head 26 may take any suitable form and should in no way be limited by the exemplary embodiments pictured in FIGS. 12A-12C.

In one embodiment, a method of making ultrasound transmission member 24 involves providing transmission member precursor material 450 (FIG. 12A), removing some of material 450 by any suitable process to form transmission member 24 and distal head 26 (FIG. 12B), and then removing additional material from distal head to form one or more fluid apertures 426 (FIG. 12C). Removing material to form transmission member may be performed via any suitable method, such as sanding, grinding, cutting or the like. Similarly, removing material to form apertures 426 may be performed via any suitable method, such as boring through distal head 26. Any analogous methods are contemplated within the scope of the invention.

Although the invention has been described above with specific reference to various embodiments and examples, it should be understood that various additions, modifications, deletions and alterations may be made to such embodiments without departing from the spirit or scope of the invention. Accordingly, it is intended that all reasonably foreseeable additions, deletions, alterations and modifications be included within the scope of the invention as defined in the following claims.

What is claimed is:

1. A method of manufacturing an ultrasound transmission member for use in an ultrasound catheter device, the method comprising:
providing a generally cylindrically-shaped transmission member material;
shaping the material to taper the transmission member from a first, wider end toward a second, narrower end, so as to form a continuous tapered region between the first, wider end and the second, narrower end;
forming a distal head at the second, narrower end, such that the tapered region extends from the first, wider end to the distal head;
positioning the tapered region within a catheter body lumen; and
fitting the distal head of the ultrasound transmission member at least partially within a distal end of the catheter body lumen.

2. A method as in claim 1, wherein providing the material comprises providing an alloy having superelastic properties.

3. A method as in claim 1, wherein shaping the material comprises grinding the material.

4. A method as in claim 1, wherein forming the distal head comprises forming a bullet-shaped head.

5. A method as in claim 1, wherein forming the distal head comprises forming at least one longitudinal aperture through the head to provide for passage of at least one of a guidewire and irrigation fluid.

6. A method as in claim 1, wherein providing the material comprises providing a material having superelastic properties.

7. A method of manufacturing an ultrasound transmission member for use in an ultrasound catheter device, the method comprising:
providing a generally cylindrically-shaped transmission member material;
shaping the material to taper the transmission member from a first, wider end toward a second, narrower end, so as to form a continuous tapered region between the first, wider end and the second, narrower end;
forming a distal head at the second, narrower end, such that the tapered region extends from the first, wider end to the distal head; and
placing a portion of the ultrasound transmission member within the catheter body lumen such that the distal head of the ultrasound transmission member is disposed outside of the catheter body lumen and the tapered region is disposed within the catheter body lumen.

8. A method of manufacturing an ultrasound transmission member for use in an ultrasound catheter device, the method comprising:

providing a unitary piece of a transmission member material;

shaping the unitary piece of material to form a distal head and a tapered region, the tapered region being continuous and extending from an end of the unitary piece of material to the distal head;

positioning the tapered region within a catheter body lumen; and fitting the distal head of the ultrasound transmission member at least partially within a distal end of the catheter body lumen.

* * * * *